(12) United States Patent
Al-Oboudi

(10) Patent No.: US 8,409,121 B1
(45) Date of Patent: Apr. 2, 2013

(54) DYNAMIC MANUAL ELBOW AND KNEE FLEXION-EXTENSION ASSIST DEVICE

(76) Inventor: Waleed Al-Oboudi, La Jolla, CA (US)

( * ) Notice: Subject to any disclaimer, the term of this patent is extended or adjusted under 35 U.S.C. 154(b) by 801 days.

(21) Appl. No.: 12/329,506

(22) Filed: Dec. 5, 2008

Related U.S. Application Data

(60) Provisional application No. 60/992,649, filed on Dec. 5, 2007.

(51) Int. Cl.
*A61F 5/37* (2006.01)
*A61F 5/00* (2006.01)
*A61F 13/06* (2006.01)
*A61B 19/00* (2006.01)
*A63B 21/00* (2006.01)
*A63B 21/06* (2006.01)
*A63B 21/068* (2006.01)
*A63B 21/08* (2006.01)

(52) U.S. Cl. .......... 602/16; 128/846; 128/869; 128/870; 128/878; 128/881; 128/882; 482/92; 482/93; 482/95; 482/97; 482/131; 482/132; 482/133; 482/134; 602/5; 602/20; 602/23; 602/26; 602/61; 602/62

(58) Field of Classification Search ............... 602/5, 16, 602/20, 23, 26, 60, 61, 62; 128/846, 869, 128/870, 878, 881, 882; 482/92, 93, 95, 482/97, 131, 132, 133, 134
See application file for complete search history.

(56) References Cited

U.S. PATENT DOCUMENTS

| | | | | |
|---|---|---|---|---|
| 4,784,121 A * | 11/1988 | Brooks | ........................... | 601/34 |
| 4,801,138 A * | 1/1989 | Airy et al. | ..................... | 482/112 |
| 4,844,454 A * | 7/1989 | Rogers | .......................... | 482/131 |
| 5,122,106 A * | 6/1992 | Atwood et al. | ............... | 482/131 |
| 5,236,333 A * | 8/1993 | Barba, Jr. | ........................ | 601/34 |
| 5,342,288 A * | 8/1994 | Lee et al. | .......................... | 602/5 |
| 5,407,420 A * | 4/1995 | Bastyr et al. | ..................... | 602/5 |
| 5,662,562 A * | 9/1997 | Wohlenberg | .................... | 482/91 |
| 6,203,473 B1* | 3/2001 | Atwood | .......................... | 482/95 |
| 6,245,034 B1* | 6/2001 | Bennett et al. | .................. | 602/20 |
| 6,821,262 B1* | 11/2004 | Muse et al. | ..................... | 602/26 |
| 7,309,305 B2* | 12/2007 | Nichols | .......................... | 482/148 |
| 7,416,520 B1* | 8/2008 | Danowski | ...................... | 482/127 |
| 7,473,234 B1* | 1/2009 | Weltner et al. | ................... | 602/16 |
| 7,762,936 B2* | 7/2010 | Conley et al. | .................. | 482/131 |
| 7,806,811 B1* | 10/2010 | Danowski | ..................... | 482/127 |
| 7,946,971 B2* | 5/2011 | Conley et al. | ................. | 482/131 |

* cited by examiner

*Primary Examiner* — Michael Brown
*Assistant Examiner* — Brandon Jackson
(74) *Attorney, Agent, or Firm* — Knobbe Martens Olson & Bear, LLP

(57) ABSTRACT

A therapy tool designed to assist therapist to manually control and facilitate patient elbow and knee flexion-extension during walking, sit to stand, control in standing, and other functions is provided. The therapy tool includes a first cushion adapted to receive at least a portion of a person's shin or forearm, a second cushion adapted to cushion a person's knee, a elongate handle attached the first and second cushions in a manner such that the second cushion is disposed above the first cushion, and a horizontal extension adapted to provide a support surface for the patient.

6 Claims, 13 Drawing Sheets

DYNAMIC MANUAL ELBOW AND KNEE FLEXION-EXTENSION ASSIST DEVICE

CROSS-REFERENCE TO RELATED APPLICATIONS

This application claims the benefit of priority under 35 U.S.C. §119(e) of U.S. Provisional Application No. 60/992,649 filed on Dec. 5, 2007 and entitled DYNAMIC MANUAL ELBOW AND KNEE FLEXION-EXTENSION ASSIST, the entirety of which is incorporated herein by reference.

BACKGROUND OF THE INVENTION

1. Field of the Invention

The present invention relates generally to therapy tools and, in particular, concerns a therapy tool for use in facilitating elbow and knee flexion-extension during sit to stand, walking, and standing for individuals suffering from muscle spasticity, weakness of muscle, and other symptoms of neurological disorders.

2. Description of the Related Art

Patients with neurological disorders often suffer from muscle spasticity and weakness of muscle, which are usually caused by damage to the systems that control voluntary muscle movements. Spasticity is demonstrated when muscles receive improper nerve signals causing them to involuntarily contract. In weakness of muscle, the systems which control motor function are damaged, resulting in paralysis and degeneration of muscle. Improper control of brain signals is often due to damage within the brain caused by stroke, brain injury, or other traumas. Often times, patients with muscle spasticity or weakness of muscles need assistance with certain movements such as knee or elbow flexion and extension. To this end, there is a particular need for a therapy device which provides assistance by facilitating patient elbow and knee flexion-extension during walking, sit to stand, standing, and other functions.

SUMMARY OF THE INVENTION

The devices, methods, and systems of the invention each have several aspects, no single one of which is solely responsible for its desirable attributes. Without limiting the scope of this invention, its more prominent features will now be discussed briefly. After consideration of this discussion and particularly after reading the section entitled "Detailed Description of Certain Embodiments," one will understand how the features of this invention provide advantages that include, for example, lower cost, ease of manufacture, and ease of use.

A preferred embodiment of the present invention provides a dynamic manual elbow and knee flexion-extension assist therapy tool. The therapy tool is designed to aid therapists in assisting with knee flexion-extension during sit to stand, facilitating walking and various activities that require elbow movements. Preferably, the therapy tool can be used by therapists to manually control and facilitate patient elbow and knee flexion-extension during walking, sit to stand, control in standing, other functions in upright postures and various activities requiring elbow flexion-extension. The tool can also be used to directly control various shoulder movements.

Another preferred embodiment of the present invention provides a dynamic manual elbow and knee flexion-extension assist therapy device. The device comprises a first cushion adapted to receive at least a portion of a person's shin or forearm, a second cushion adapted to cushion a person's knee, a elongate handle attached the first and second cushions in a manner such that the second cushion is disposed above the first cushion; and a horizontal extension adapted to provide a support surface for the patient.

In one implementation, the therapy tool comprises a well-cushioned part adapted to fit over the shin area of a patient's leg or the patient's forearm, a plurality of straps for secure comfortable fastening, an elongate handle that can be adjustable in height to accommodate the therapist's reach and the patient's leg or arm length, and a well-cushioned attachment to the handle and adapted to fit over the patient's patella to protect it and help with knee extensions.

In another implementation, various optional accessory attachments can be attached to the elongate handle, including straps that connect the handle to the patient's thigh (femur) or upper arm (humerus). These accessory straps can help define the parameter of elbow, and knee flexion and extension. Other accessory attachments can include a surface that fits at the end of the elongate handle to help position the patient's affected hand during sit to stand and stand to sit practice. In addition, some attachments can include an L-shaped bar that attaches to the elongate handle and can be used by patient to help control knee flexion-extension. Also, handle extensions are available to help in cueing the patient's upper body and lower body alignment when the tool is worn on the lower extremely during walking. Other optional accessory attachments can attach to the part covering the shin or forearm area that helps with foot or hand facilitation and alignment.

DETAILED DESCRIPTION OF THE PREFERRED EMBODIMENT

Figure 1:
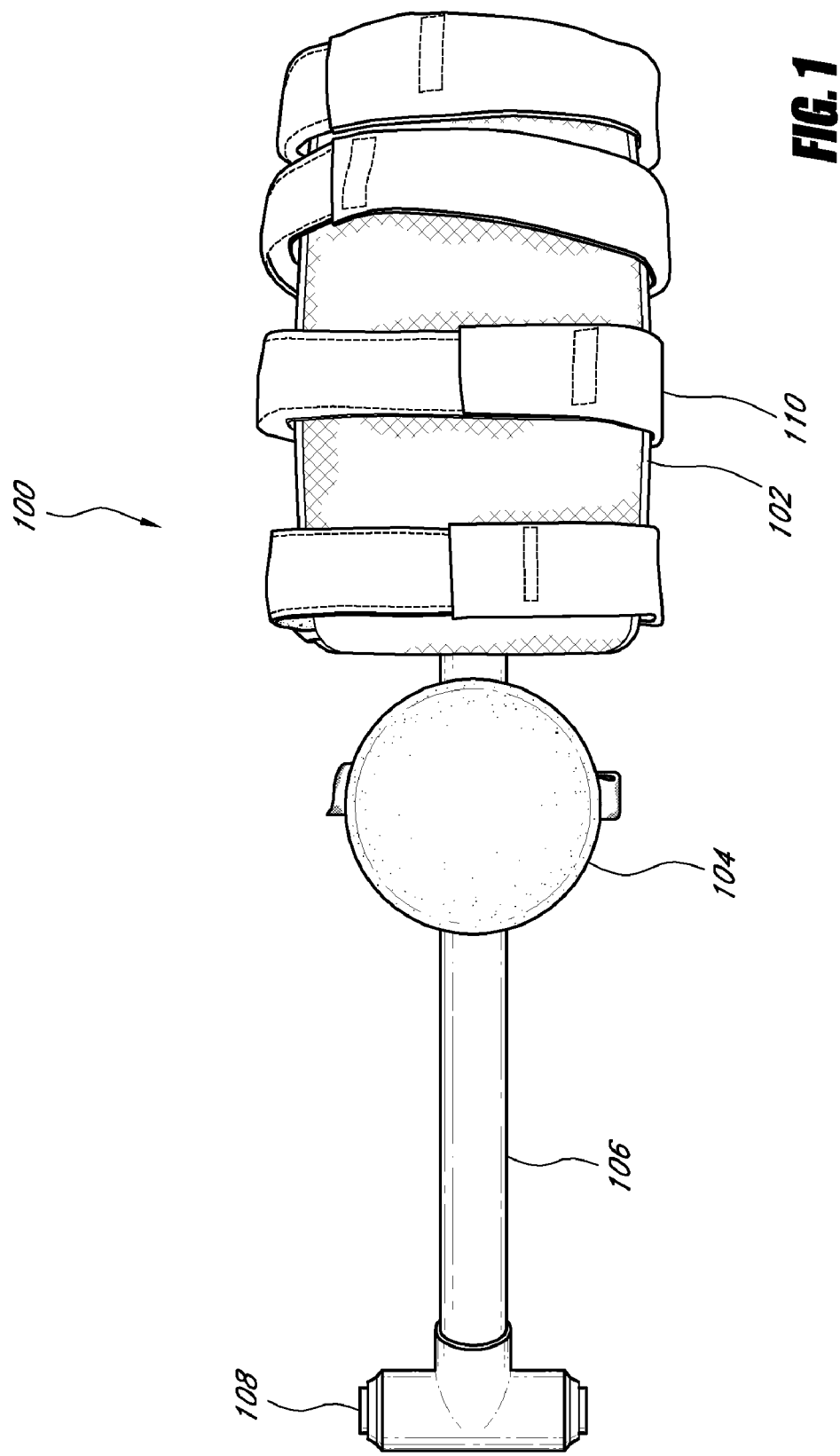
FIG. 1 is a front view of a dynamic manual elbow and knee flexion-extension assist device of one embodiment of the present invention.

FIG. 1 illustrates a dynamic manual elbow and knee flexion-extension assist device 100 adapted to aid therapists in assisting with knee or elbow flexion-extension and facilitating walking and various activities. The device can be worn around the lower leg or forearm of the patient.

As shown in FIG. 1, the device 100 generally comprises a first cushion 102 and a second cushion 104 attached to an elongate support 106. The first cushion 102 has a generally rectangular in shape and is configured to receive at least a portion of a person's lower leg or forearm. The second cushion 104 is preferably smaller in area and positioned above the first cushion 102. In one embodiment, the first cushion 102 is contoured to fit around at least a portion of a person's shin or forearm and the second cushion 104 is contoured to protect or cushion the patella. The device 100 further includes a connecting point 108 disposed on an end of the elongate support 106. In one embodiment, the connecting point 108 comprises a T-joint. In certain preferred embodiments, the elongate support 106 is made of a light plastic material and yet sufficiently rigid to support a person's weight. In other embodiments, the elongate support is adjustable in height to accommodate the therapist's reach. A plurality of straps 110 are preferably attached to the first cushion and adapted to wrap around a person's lower leg or forearm.

Figure 2:
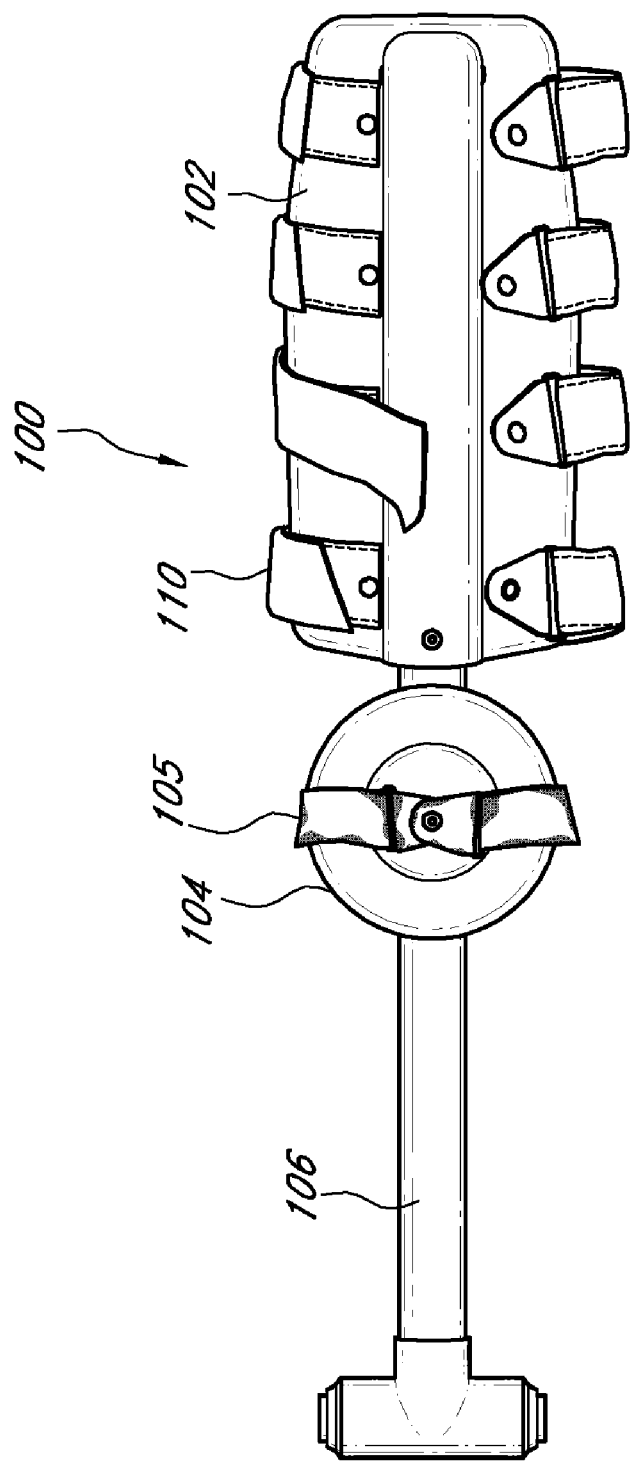
FIG. 2 is a rear view of the dynamic manual elbow and knee flexion-extension assist device of FIG. 1.
Figure 3:
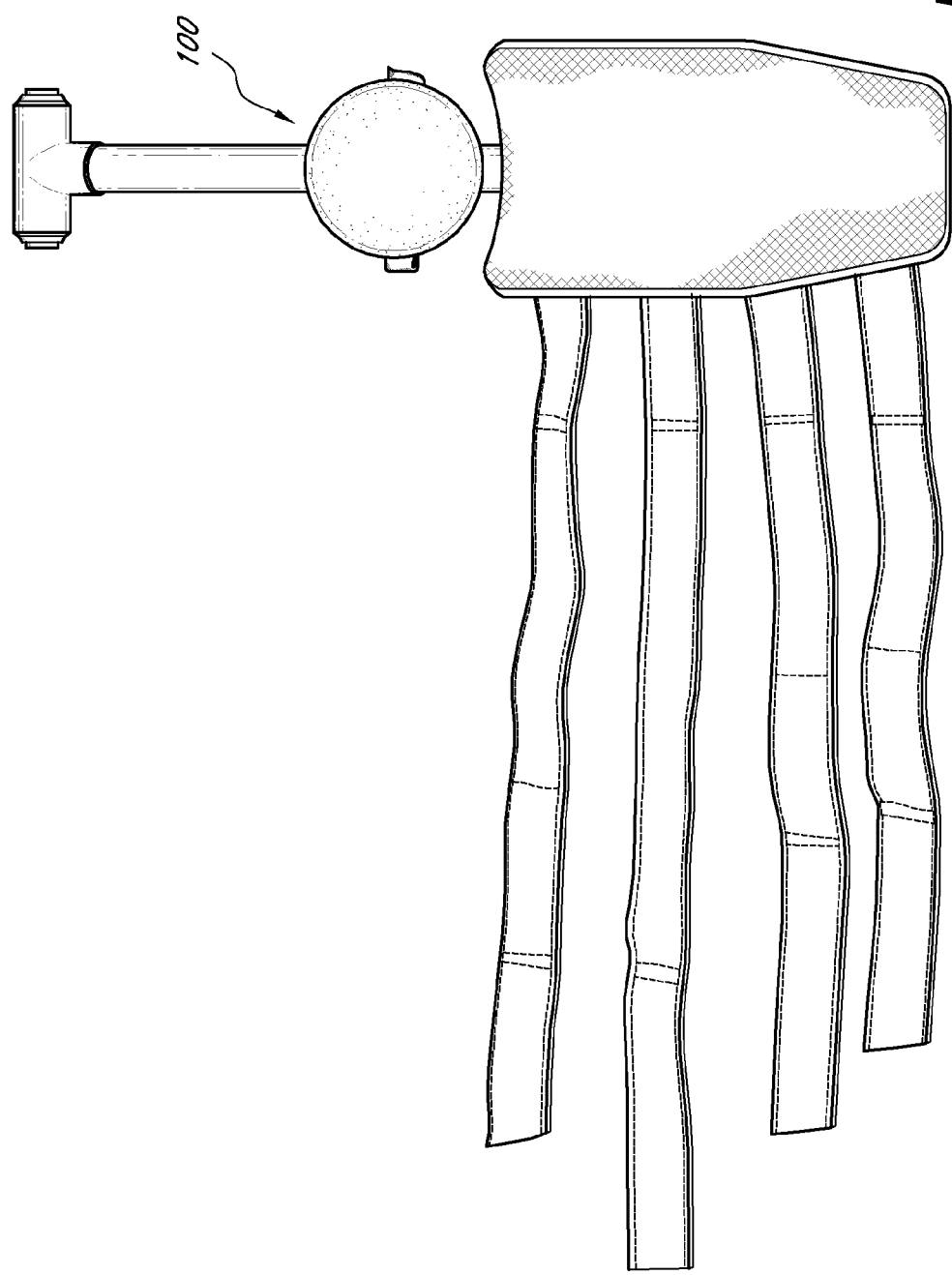
FIG. 3 is a front view of the dynamic manual elbow and knee flexion-extension assist device of FIG. 1 showing the straps extending laterally from the cushion.
Figure 4:
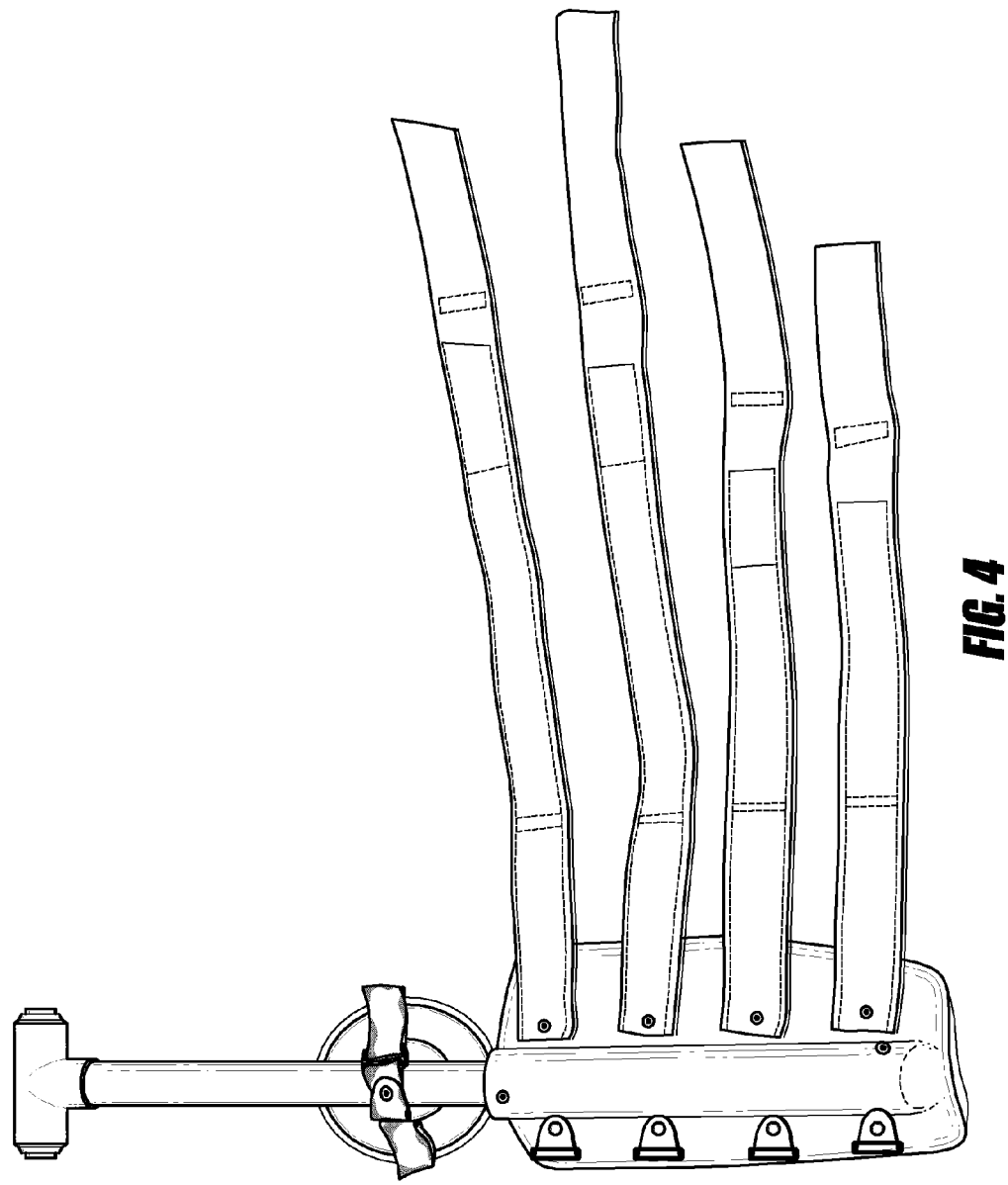
FIG. 4 is a rear view of the dynamic manual elbow and knee flexion-extension assist device of FIG. 1 showing the straps extending laterally from the cushion.

FIG. 2 illustrates a rear view of the device 100. As shown in FIG. 2, the straps 110 are fixedly attached to the back side of the first cushion 102. As also shown in FIG. 2, the second cushion 104 is attached to the elongate support 106 by a strap 105 fixedly attached to the back side of the elongate support. In one embodiment, adjustment clips are used to adjust the length of the straps 110 when they are wrapped around a person's leg or arm. In another embodiment, hook and loop attachment means can be used to fasten the straps on the person's arm or leg. FIG. 3 shows the device 100 with the straps 110 unfastened. FIG. 4 illustrates a rear view of the device 100 with the straps unfastened.

Figure 5:
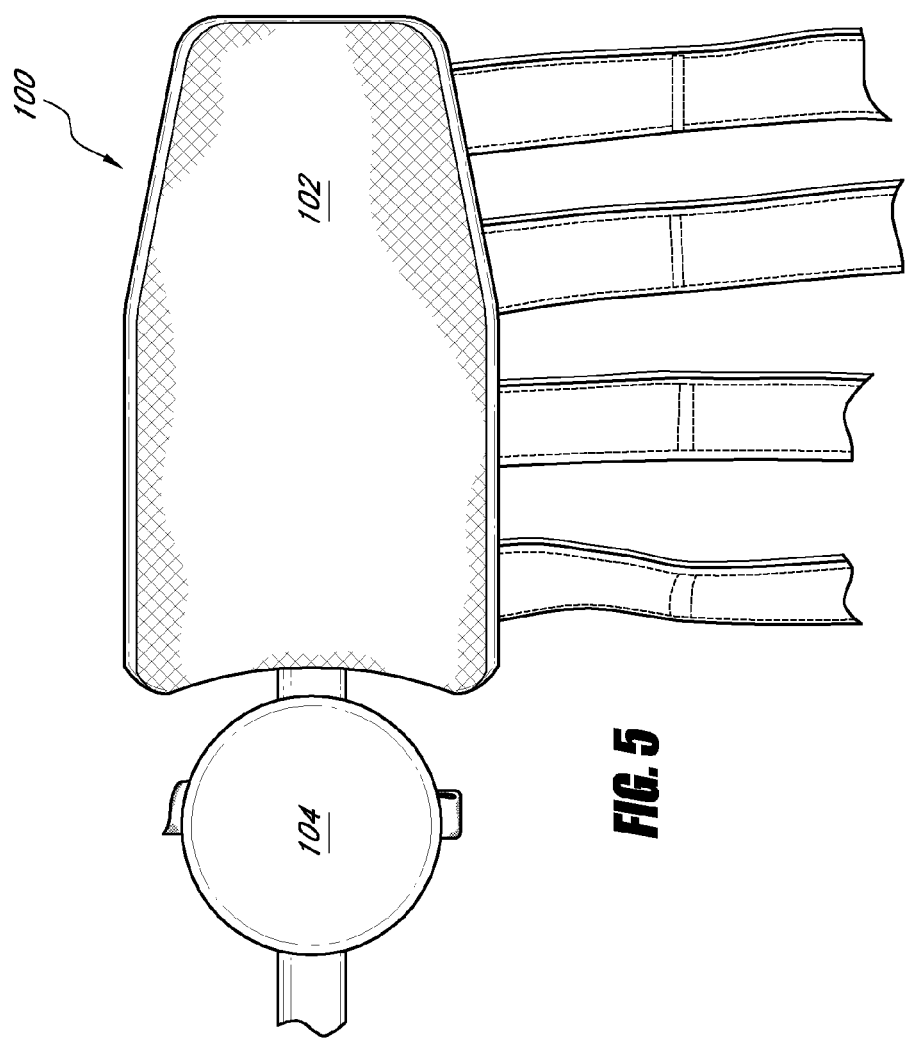
FIG. 5 is a partial view of the dynamic manual elbow and knee flexion-extension assist device of FIG. 1, showing a first cushion contoured to receive a portion of the shin or forearm and a second cushion adapted to protect the patella or elbow.
Figure 6:
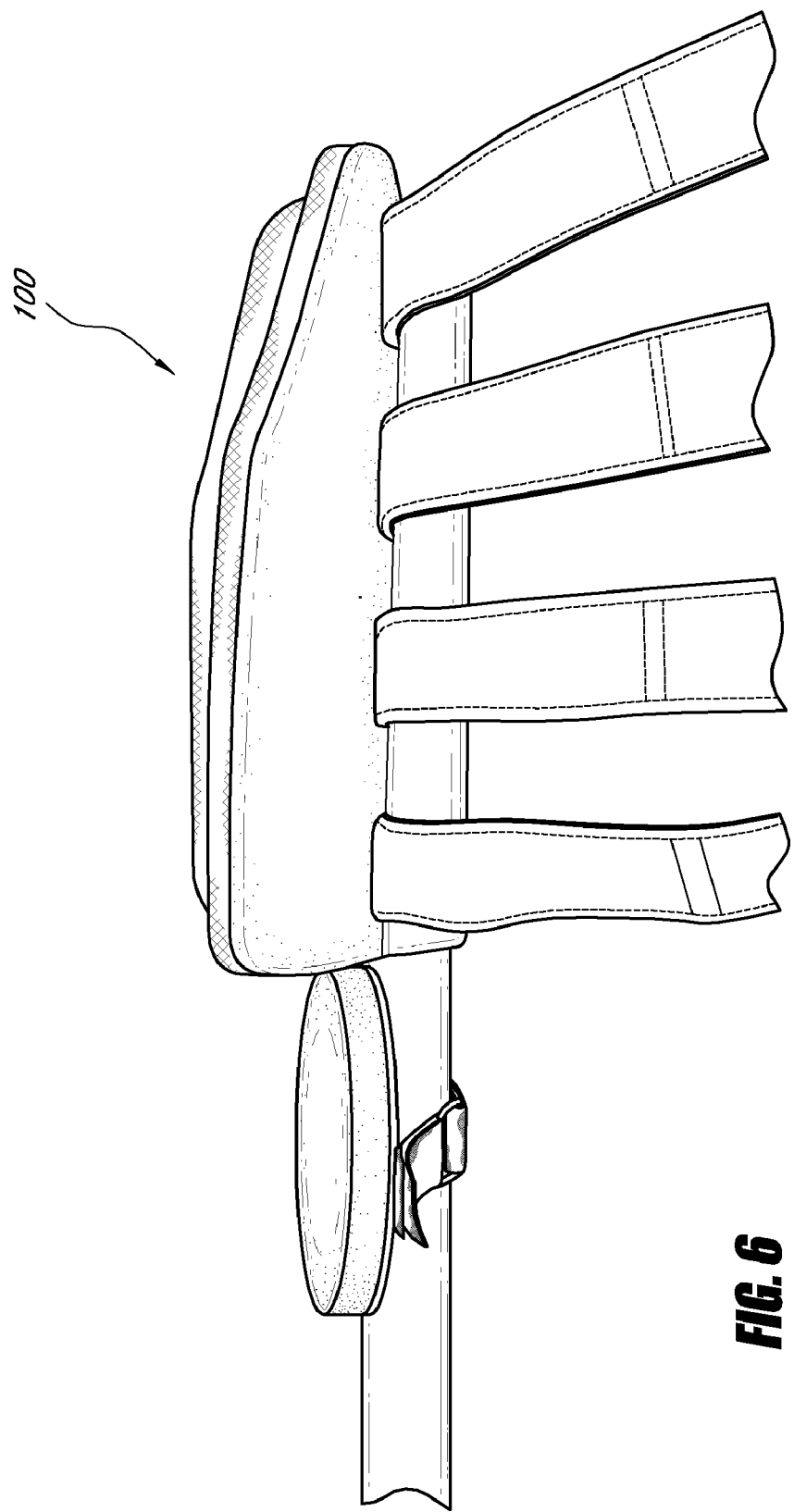
FIG. 6 is a side view of the dynamic manual elbow and knee flexion-extension assist device of FIG. 1.

FIG. 5 is a partial view of the dynamic manual elbow and knee flexion-extension assist device 100, showing the first cushion 102 contoured to receive a portion of the shin or forearm and the second cushion 104 adapted to protect the patella or elbow. FIG. 6 is a side view of the device 100.

Figure 7:
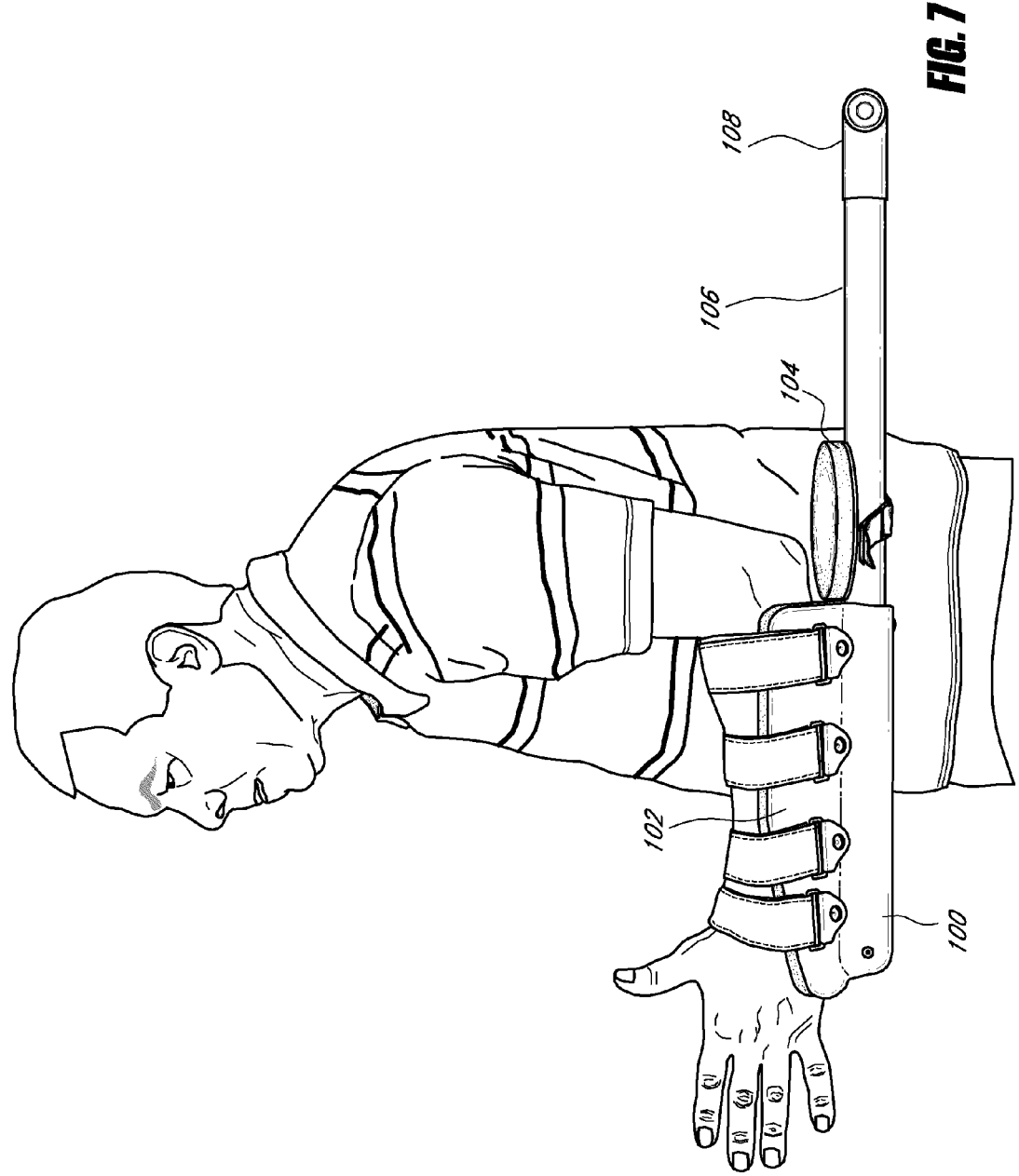
FIG. 7 illustrates the manner in which the device of FIG. 1 can be worn around the patient's forearm.

FIG. 7 illustrates the manner in which the device 100 can be used to assist elbow flexion-extension. As shown in FIG. 7, the device 100 is strapped to a patient's forearm with the forearm positioned against the contoured inner surface of the first cushion 102. Preferably, the device 100 is configured such that when the patient's forearm is fitted inside the first cushion 102, the patient's elbow is positioned against the second cushion 104. In certain embodiments, the therapist can control movement of the patient's elbow movement by manipulating the handle 108 of the device 100. Advantageously, the handle 108 of the elongate support 106 extends outwardly beyond the person's elbow so as to allow the therapist facilitate the patient's elbow flexion-extension by moving the handle 108.

Figure 8:
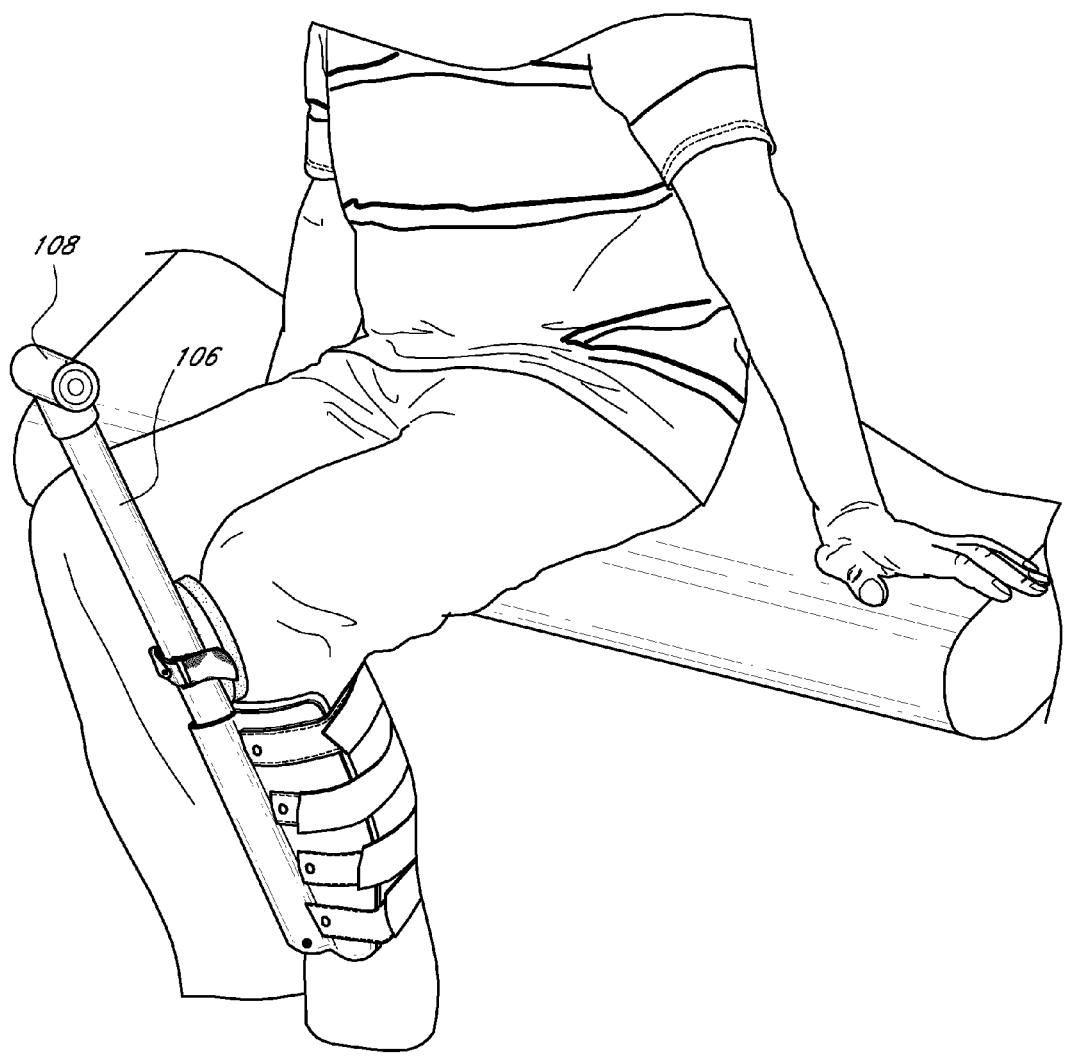
FIG. 8 illustrates the manner in which the device of FIG. 1 can be worn around the patient's shin.
Figure 9:
FIG. 9 illustrates the manner in which the device of FIG. 1 can assist a patient to move from a sit to stand position.
Figure 10:
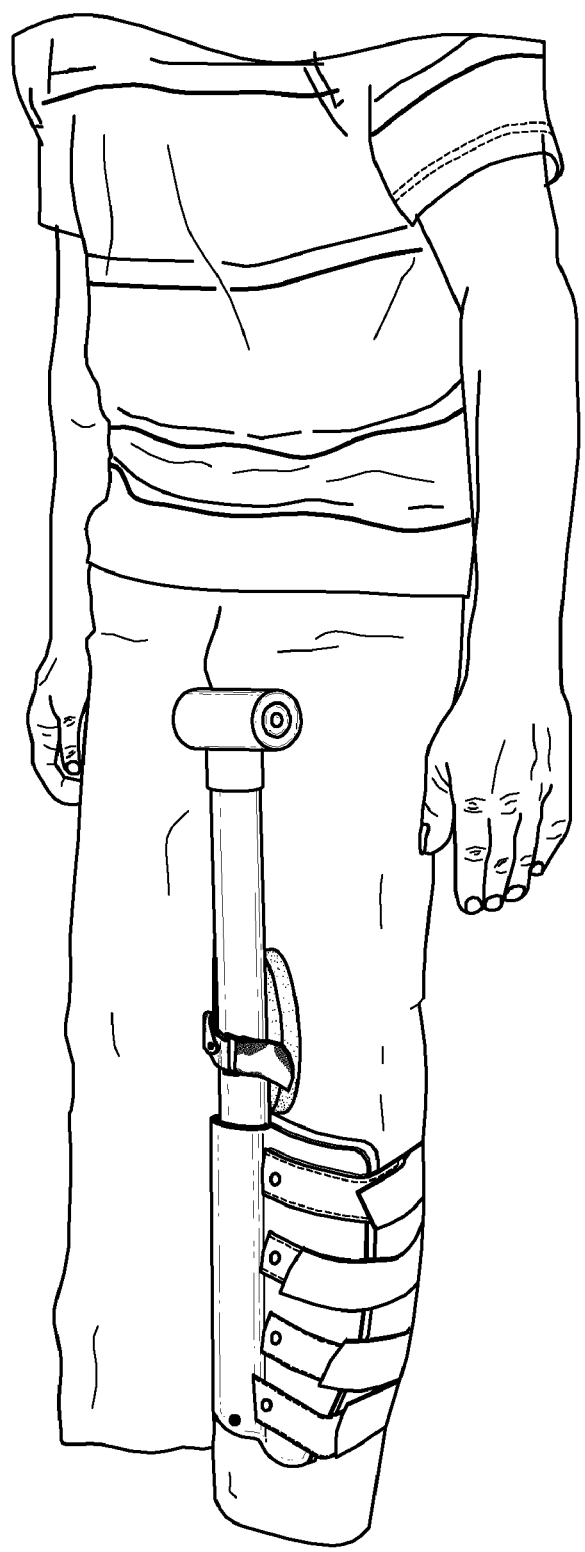
FIG. 10 illustrates the manner in which the device of FIG. 1 can support a patient in a standing position.

FIGS. 8-10 illustrates the manner in which the device facilitates the patient's knee flexion-extension. As shown in FIG. 8, the device is attached to the patient's lower leg with the elongate support 106 extending upwardly so that the patient has ready access to the handle 108 for support.

Figure 11:
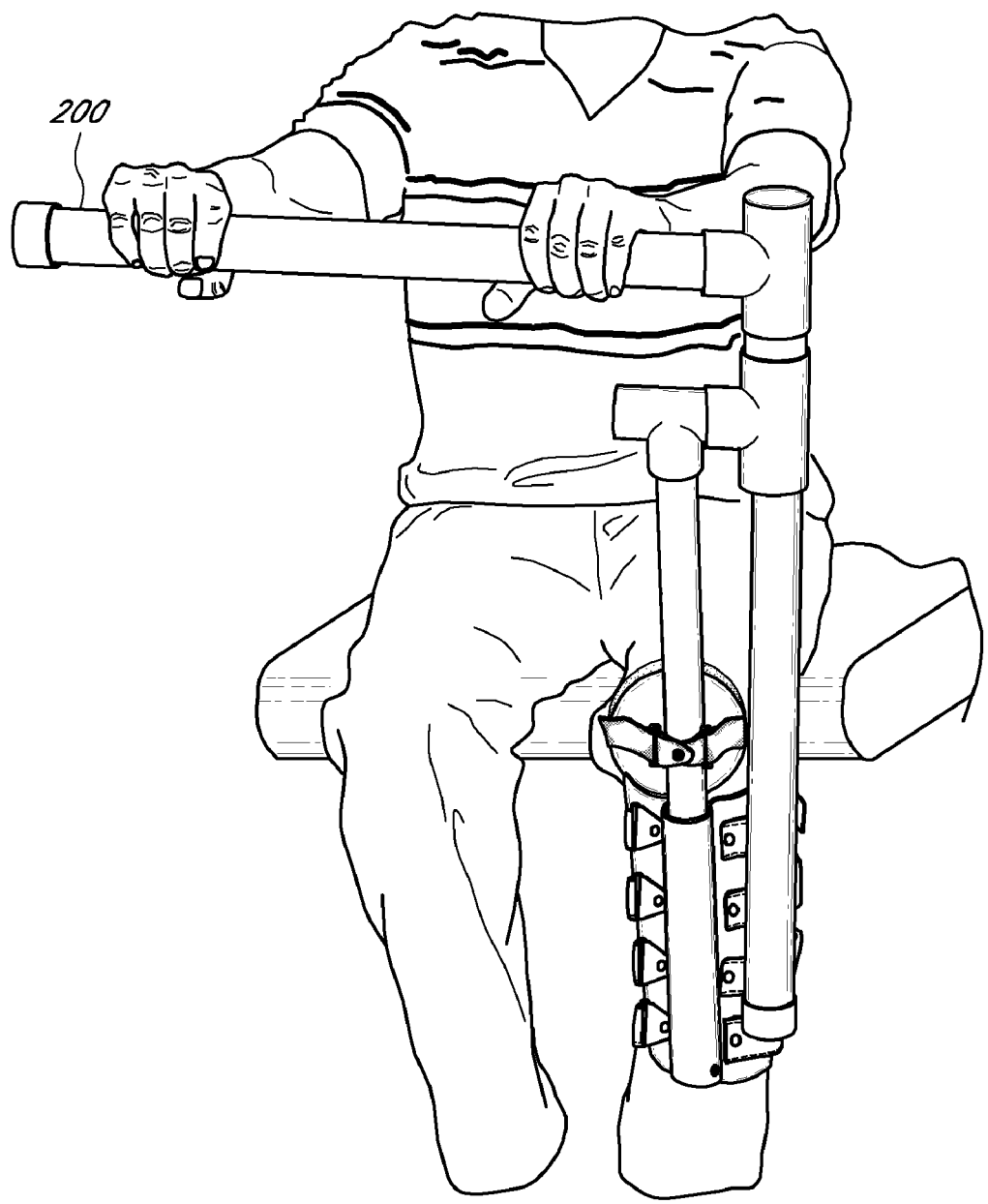
FIG. 11 illustrates the device of FIG. 1 having a horizontal extension attached to an end of the handle to assist the patient move from a sit to stand position or stand to sit position.
Figure 12:
FIG. 12 illustrates the manner in which the device of FIG. 11 can be used by a patient when moving from a sit to stand position.
Figure 13:
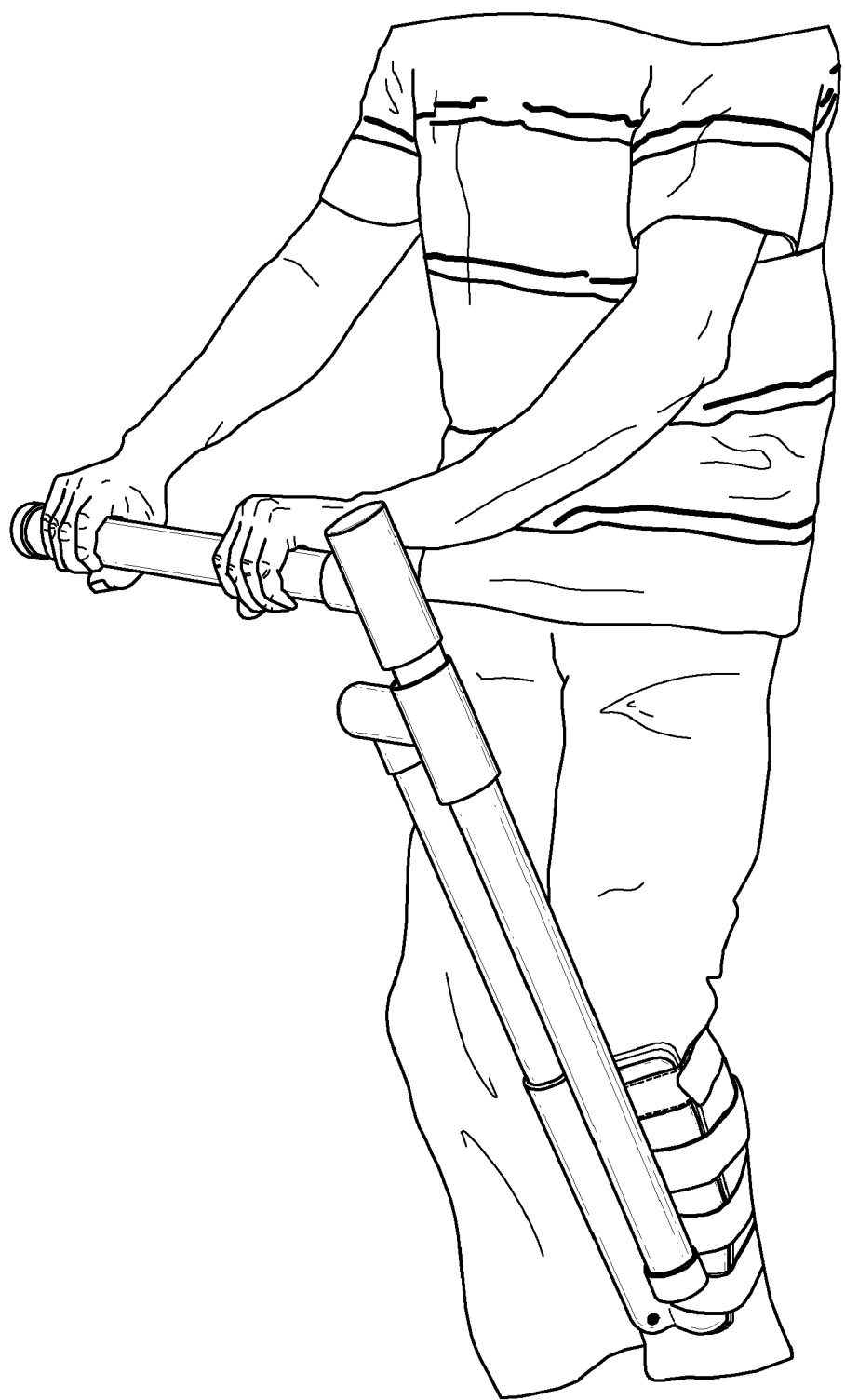
FIG. 13 illustrates the manner in which the device of FIG. 11 can be used by a patient.

FIGS. 11-13 show another embodiment of the device wherein a horizontal extension 200 is connected to the device to provide a supporting surface for the patient. Preferably the horizontal extension can assist the patient in moving from a sit to stand or stand to sit position. In one embodiment, the horizontal extension 200 is configured to telescope into the T-joint. The horizontal extension 200 further serves to help position the patient's affected hand during sit to stand and stand to sit practices. In one embodiment, a D-ring is positioned on the front of the first cushion for attaching straps or other elastic components thereto.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separated from others.

What is claimed is:

1. A therapy tool, comprising:
    an elongate support, wherein said elongate support is adjustable in length;
    a connecting joint disposed on an end of the elongate support, said connecting joint comprising a T joint;
    a first cushion coupled to a lower portion of the elongate support, wherein the first cushion has an extended contoured inner surface adapted to conform to the front of a person's shin or forearm;
    a second cushion coupled to a middle portion of the elongate support and adapted to conform to a person's knee or elbow;
    a plurality of straps adapted to attach the first cushion to the person's knee or forearm; and
    and a horizontal handle disposed on an upper end of the elongate support, wherein the horizontal handle is adapted to telescope into the connecting joint.

2. The therapy tool of claim 1, further comprising an L-shaped bar, said L-shaped bar being attached to the elongate handle.

3. The therapy tool of claim 1 wherein the elongate support is made of a plastic material.

4. The therapy tool of claim 1 wherein at least one of the plurality of straps is attached to the backside of the first cushion.

5. The therapy tool of claim 1 wherein the plurality of straps comprises hook and loop attachment fasteners.

6. A method of manually controlling and facilitating a patient's knee flexion-extension, comprising:
    attaching a first cushion to a front surface of the person's shin, wherein the first cushion comprises an extended contoured inner surface adapted to conform to the front surface of the person's shin;
    attaching a second cushion to the person's patella;
    providing an elongate upright and a horizontal extension disposed on the elongate upright, wherein the elongate upright extends upwardly when the first cushion is attached to the front surface of the person's shin, wherein the elongate upright provides a support for the person;
    telescoping the horizontal extension from the elongate upright to a pre-selected length,
    positioning the patient's hands on the horizontal extension.

* * * * *